(12) United States Patent
Whitney et al.

(10) Patent No.: US 11,229,508 B2
(45) Date of Patent: Jan. 25, 2022

(54) SELF-DISINFECTING TEETH-WHITENING DEVICE

(71) Applicant: Foresold LLC, Phoenix, AZ (US)

(72) Inventors: Jason Lynn Whitney, Big Bear City, CA (US); Steven Lee Lane, Orange, CA (US); Celina Chen, Irvine, CA (US); Joshua F. Valdez-Elizetxe, Paradise Valley, AZ (US)

(73) Assignee: Foresold LLC, Phoenix, AZ (US)

( * ) Notice: Subject to any disclaimer, the term of this patent is extended or adjusted under 35 U.S.C. 154(b) by 309 days.

(21) Appl. No.: 16/360,755

(22) Filed: Mar. 21, 2019

(65) Prior Publication Data

US 2019/0388206 A1  Dec. 26, 2019

Related U.S. Application Data (60) Provisional application No. 62/750,674, filed on Oct. 25, 2018, provisional application No. 62/750,630, (Continued)

(51) Int. Cl.
*A61C 19/06* (2006.01)
*A61C 19/02* (2006.01)
(Continued)

(52) U.S. Cl.
CPC .......... *A61C 19/066* (2013.01); *A61B 5/0088* (2013.01); *A61C 19/02* (2013.01);
(Continued)

(58) Field of Classification Search
CPC .......... A61B 5/0088; A61B 2562/0219; A61B 2562/0223; A61C 19/02; A61C 19/04;
(Continued)

(56) References Cited

U.S. PATENT DOCUMENTS 5,490,520 A    2/1996  Schaefer et al.
6,616,447 B1*  9/2003  Rizoiu ................. A61C 19/063
                                                      433/216
(Continued)

FOREIGN PATENT DOCUMENTS

WO    WO2007092368    8/2007
WO    2019/141834 A1  7/2019
(Continued)

*Primary Examiner* — Matthew M Nelson
(74) *Attorney, Agent, or Firm* — Mintz Levin Cohn Ferris Glovsky and Popeo, P.C.

(57) ABSTRACT

Devices for whitening teeth that include a mouth piece and an ultraviolet light source, a sterilizer that sterilizes the mouth piece, or at least one Hall-effect sensor. At least a portion of the device or mouth piece may be sterilized. A wireless charging system may drive the sterilizer or UV source, which may operate only when the mouth piece is not in the user's mouth or when the mouth piece is charging. A safety mechanism may protect the user from eye damage. The mouth piece may be charged while the mouth piece and UV source are in an enclosure. The UV source or sterilizer may turn on only while the mouth piece is in the enclosure or only while the enclosure is closed. The Hall-effect sensor(s) may control whether the UV source or sterilizer is on or may detect whether the mouth piece is docked within the charger.

13 Claims, 7 Drawing Sheets

Related U.S. Application Data filed on Oct. 25, 2018, provisional application No. 62/750,652, filed on Oct. 25, 2018, provisional application No. 62/750,549, filed on Oct. 25, 2018, provisional application No. 62/750,601, filed on Oct. 25, 2018, provisional application No. 62/687,632, filed on Jun. 20, 2018.

(51) Int. Cl.
  *B08B 7/00* (2006.01)
  *A61N 5/06* (2006.01)
  *A61B 5/00* (2006.01)
  *A61C 19/04* (2006.01)
  *A61Q 11/00* (2006.01)

(52) U.S. Cl.
  CPC .......... *A61N 5/0603* (2013.01); *B08B 7/0057* (2013.01); *A61B 2562/0219* (2013.01); *A61B 2562/0223* (2013.01); *A61C 19/04* (2013.01); *A61C 2204/002* (2013.01); *A61N 2005/0606* (2013.01); *A61N 2005/0652* (2013.01); *A61N 2005/0662* (2013.01); *A61Q 11/00* (2013.01)

(58) Field of Classification Search
  CPC ............ A61C 19/066; A61C 2204/002; A61N 5/0603; A61N 2005/0606; A61N 2005/0652; A61N 2005/0662; A61Q 11/00; B08B 7/0057
  USPC ........................................................ 433/216
  See application file for complete search history.

(56) References Cited

U.S. PATENT DOCUMENTS

| | | | |
|---|---|---|---|
| 7,144,249 B2 | 12/2006 | Rizoiu et al. | |
| 7,201,577 B2 | 4/2007 | Levine | |
| 7,326,055 B2 | 2/2008 | Yamaguchi et al. | |
| 7,335,025 B2 | 2/2008 | Levine | |
| 7,597,497 B2 | 10/2009 | Levine | |
| D636,074 S | 4/2011 | Levine | |
| 8,029,278 B1 | 10/2011 | Levine | |
| 8,215,954 B2 | 7/2012 | Levine | |
| 8,262,306 B2 | 9/2012 | Levine | |
| 8,267,609 B2 | 9/2012 | Levine | |
| 8,371,853 B2 | 2/2013 | Levine | |
| 8,376,746 B2 | 2/2013 | Brown et al. | |
| 9,000,398 B2 | 4/2015 | Nelson et al. | |
| 9,271,638 B2 | 3/2016 | Levine | |
| D765,255 S | 8/2016 | Levine | |
| 9,492,257 B2 | 11/2016 | Jablow et al. | |
| 9,539,075 B2 | 1/2017 | Sanders et al. | |
| 9,636,198 B2 | 5/2017 | Kodama | |
| 9,662,183 B2 | 5/2017 | Lowe et al. | |
| D795,501 S | 8/2017 | Levine | |
| 9,730,780 B2 | 8/2017 | Brawn et al. | |
| 9,827,174 B2 | 11/2017 | Levine | |
| 9,974,630 B2 | 5/2018 | Heacock et al. | |
| 10,064,711 B1 | 9/2018 | Richter et al. | |
| 10,099,064 B2 | 10/2018 | Newman et al. | |
| 10,123,860 B2 | 11/2018 | Levine | |
| 10,220,221 B2 | 3/2019 | Wu | |
| 10,398,894 B2 | 9/2019 | Johansson et al. | |
| 10,512,789 B2 | 12/2019 | Newman et al. | |
| 10,716,652 B2 | 7/2020 | Stewart et al. | |
| 10,729,524 B2 * | 8/2020 | Brawn .................. | A61C 19/06 |
| 2004/0019990 A1 * | 2/2004 | Farrell ................ | A46B 15/0081 15/105 |
| 2006/0003284 A1 | 1/2006 | Sale | |
| 2006/0019214 A1 | 1/2006 | Lawrence et al. | |
| 2006/0127837 A1 * | 6/2006 | Nguyen ............... | A61C 19/063 433/29 |
| 2006/0134576 A1 | 6/2006 | West | |
| 2006/0228158 A1 | 10/2006 | Levine | |
| 2006/0234189 A1 | 10/2006 | Duret | |
| 2007/0276455 A1 | 11/2007 | Fiset | |
| 2008/0032253 A1 | 2/2008 | Montgomery et al. | |
| 2008/0233541 A1 | 9/2008 | De Vreese | |
| 2011/0076636 A1 | 3/2011 | Wolff | |
| 2011/0091835 A1 | 4/2011 | Levine | |
| 2011/0104631 A1 | 5/2011 | Levine | |
| 2011/0189626 A1 | 8/2011 | Sanzari | |
| 2011/0198626 A1 | 8/2011 | Edmond | |
| 2012/0183919 A1 | 7/2012 | Levine | |
| 2013/0045457 A1 | 2/2013 | Chetiar et al. | |
| 2014/0329192 A1 * | 11/2014 | Kaskoun ................ | A61B 5/682 433/6 |
| 2015/0164618 A1 * | 6/2015 | Heacock .................. | A61C 7/08 433/6 |
| 2015/0216642 A1 * | 8/2015 | Ajiki ..................... | A61C 1/0007 433/27 |
| 2015/0257863 A1 | 9/2015 | Gatzemeyer et al. | |
| 2015/0306486 A1 * | 10/2015 | Logan ................ | A61B 5/14551 600/301 |
| 2016/0220013 A1 | 8/2016 | Barnes et al. | |
| 2017/0116665 A1 | 4/2017 | Alzahrani | |
| 2017/0173358 A1 * | 6/2017 | Demarest ............. | A61N 5/0624 |
| 2017/0224455 A1 * | 8/2017 | Levine ............... | A61B 5/14507 |
| 2017/0231735 A1 * | 8/2017 | Young ................. | A61N 5/0603 433/29 |
| 2017/0238863 A1 * | 8/2017 | Kimmel ............... | A61B 5/0507 |
| 2017/0249445 A1 | 8/2017 | Devries et al. | |
| 2017/0252140 A1 | 9/2017 | Murphy et al. | |
| 2017/0312118 A1 * | 11/2017 | De Heer ................ | A62B 23/06 |
| 2018/0071065 A1 | 3/2018 | Flyash et al. | |
| 2018/0140406 A1 * | 5/2018 | Brawn .................... | A61C 19/06 |
| 2018/0206957 A1 * | 7/2018 | Ruth .................... | A61C 9/0013 |
| 2018/0263746 A1 * | 9/2018 | Demarest ............. | A61N 5/0603 |
| 2019/0167400 A1 | 6/2019 | Barnes et al. | |
| 2019/0388204 A1 | 12/2019 | Whitney et al. | |
| 2019/0388205 A1 | 12/2019 | Whitney et al. | |
| 2019/0388207 A1 | 12/2019 | Whitney et al. | |
| 2019/0388208 A1 | 12/2019 | Whitney et al. | |
| 2020/0230432 A1 | 7/2020 | Jablow | |

FOREIGN PATENT DOCUMENTS

| | | |
|---|---|---|
| WO | 2019/234308 A1 | 12/2019 |
| WO | 2020/123992 A1 | 6/2020 |

* cited by examiner

SELF-DISINFECTING TEETH-WHITENING DEVICE

RELATED PATENT APPLICATIONS

This patent application is a non-provisional patent application of, and claims priority to:

U.S. provisional patent application No. 62/687,632, filed Jun. 20, 2018, TEETH WHITENING DEVICE;

U.S. provisional patent application No. 62/750,549, filed Oct. 25, 2018, TEETH WHITENING WITH EXTERNAL OR CONTROLLED LIGHT SOURCE;

U.S. provisional patent application No. 62/750,601, filed Oct. 25, 2018, COLOR OR SHADE SENSING TEETH-WHITENING DEVICE;

U.S. provisional patent application No. 62/750,630, filed Oct. 25, 2018, SELF-DISINFECTING TEETH-WHITENING DEVICE;

U.S. provisional patent application No. 62/750,652, filed Oct. 25, 2018, MOUTH-DETECTING TEETH WHITENING DEVICE; and U.S. provisional patent application No. 62/750,674, filed Oct. 25, 2018, CONNECTED TEETH WHITENING DEVICE.

The contents of these priority provisional patent applications are incorporated herein by reference. If there are any conflicts or inconsistencies between this patent application and the incorporated provisional patent applications, however, this patent application governs herein.

FIELD OF THE INVENTION

Various embodiments of this invention relate to devices and methods for whitening teeth including electronic devices and devices and methods that use a source of light to whiten teeth.

BACKGROUND OF THE INVENTION

In the past, various devices and methods have been used to whiten teeth including electronic devices that use light to whiten the teeth. Various problems encountered in prior technology are described herein. Needs or potential for benefit exist for better devices, including, electronic devices, and methods that whiten teeth. Room for improvement exists over the prior art in these and other areas that may be apparent to a person of skill in the art having studied this document.

SUMMARY OF PARTICULAR EMBODIMENTS OF THE INVENTION

This invention provides, among other things, devices, methods, and systems that whiten teeth, including electronic devices and devices and methods that use light to whiten teeth. Various embodiments provide, for example, as an object or benefit, that they partially or fully address or satisfy one or more of the needs, potential areas for benefit, or opportunities for improvement described herein or known in the art, as examples. Certain embodiments provide, for example, as objects or benefits, for instance, that they whiten teeth, for example, using light. Various embodiments are better than prior art alternatives in one or more ways, for instance, as described herein. Various embodiments are described herein or would be apparent to a person of ordinary skill in the art having studied this document.

Various embodiments are or include, for example, devices for whitening teeth of a user. Specific embodiments include, for instance, a light source and a light delivery mechanism, for example, that delivers light from the light source to the user's teeth. In some embodiments, for example, when the device is being used to whiten the teeth of the user, the light source is located outside the mouth of the user. Further, in certain embodiments, when the device is being used to whiten the teeth of the user, the light delivery mechanism is located inside the mouth of the user. Further still, in particular embodiments, the light delivery mechanism is or includes a reflector. Even further, some embodiments include a pulse width modulation circuit, for example, that drives the light source. Still further, in particular embodiments, the light source includes multiple LEDs, multiple independently-controlled light sources, or both, as examples. Even further still, in certain embodiments intensity of the light source is controlled, the device is controlled wirelessly using a separate electronic device, the device is controlled using hand gestures, the device includes a gesture sensor that senses hand gestures, or a combination thereof, as examples. Moreover, in particular embodiments, the device for whitening teeth includes two antennas, an infrared receiver, or both (e.g., to detect hand gestures).

Numerous specific embodiments of a device for whitening teeth of a user include both a light source and a reflector. Further, in a number of embodiments, when the device is being used to whiten the teeth of the user, the light source is located outside the mouth of the user and the reflector is located inside the mouth of the user. Still further, various specific embodiments of a device for whitening teeth of a user include a light source and a pulse width modulation circuit, for instance, that drives the light source. Even further, in particular embodiments, the light source includes multiple light sources, for instance, that are each independently controlled, for example, by the pulse width modulation circuit. Even further still, in certain embodiments, the device is controlled wirelessly using a separate electronic device, using hand gestures, or both, as examples.

For many specific embodiments of devices for whitening the teeth of a user, the device includes a color sensor, for example, that detects color of the teeth of the user. Further, in a number of embodiments, the device controls a teeth-whitening process, for instance, using the color of the teeth of the user, the device for whitening teeth includes a processor, for example, that controls the teeth-whitening process, for instance, using the color of the teeth of the user, or a combination thereof. Still further, in various embodiments, the device includes a light source, for example, that emits light that is reflected by the teeth, and used, for instance, by the device, to detect the color of the teeth of the user. Moreover, in various embodiments, the device includes a light source, for example, that shines light on the teeth, for instance, to whiten the teeth. Even further, in some embodiments, the device uses the color of the teeth to determine, for example, intensity of light to shine onto the teeth. Further still, in particular embodiments, the device includes cool light source elements, warm light source elements, or both. Even further still, in certain embodiments, the device includes multiple color sensors, and, in particular embodiments, different color sensors of the multiple color sensors sense color of the teeth of the user in different areas of the mouth of the user. Further, in other embodiments, shade sensors are used in addition to, or instead of, color sensors, and shade of the teeth is used.

In some embodiments, the device uses a learning algorithm, for example, to determine a teeth-whitening process, for instance, using the color of the teeth of the user. Further, in certain embodiments, the device for whitening teeth includes multiple independently-controlled light sources. Still further, in particular embodiments, the device for whitening teeth includes a light source and a reflector and (e.g., when the device is being used to whiten the teeth of the user) the light source is located outside the mouth of the user, the reflector is located inside the mouth of the user, or both. Further still, in various embodiments, the device for whitening teeth includes a pulse width modulation circuit, the device is controlled wirelessly (e.g., using a separate electronic device), the device includes a gesture sensor (e.g., that senses hand gestures used to control the device), or a combination thereof, as examples.

In many specific embodiments of a device for whitening teeth of a user, the device collects data from light that is reflected from the teeth and controls a teeth-whitening process using the data. In a number of embodiments, for example, the data includes color of the teeth and the device uses the color of the teeth to control the teeth-whitening process. Further, in some embodiments, for example, the data includes shade of the teeth and the device uses the shade of the teeth to control the teeth-whitening process. Further still, in many embodiments, the teeth-whitening process includes shining light on the teeth to whiten the teeth. Still further, in various embodiments, a device for whitening teeth of a user includes (e.g., color, shade, or both) sensors, for example, used to analyze reflected light from a target surface of the teeth, for instance, to recommend a whitening treatment for the teeth. Even further, in a number of embodiments, the device produces the light that becomes the reflected light when reflected by the target surface of the teeth. Even further still, in some embodiments, the device includes a processor that controls the device.

Various specific embodiments of a device for whitening teeth include a mouth piece and an ultraviolet light source. In many embodiments, for example, the ultraviolet light source sterilizes at least a portion of the device. In particular, in a number of embodiments, the ultraviolet light source sterilizes at least a portion of the mouth piece. Further, in various embodiments, the ultraviolet light source operates only when the mouth piece is not in the user's mouth, when the mouth piece is charging, or both. In a number of embodiments, for example, the device includes a wireless charging system. Even further, in certain embodiments, the wireless charging system drives the ultraviolet light source. Further still, in some embodiments, the ultraviolet light source includes at least one LED that emits the ultraviolet light. Even further still, in some embodiments, the device further includes a safety mechanism, for example, that protects the user, for instance, from eye damage from the ultraviolet light source. Still further, in some embodiments, the device for whitening teeth includes an enclosure. In a number of embodiments, for example, the mouth piece is charged while the mouth piece is in the enclosure, while the ultraviolet light source is located in the enclosure, or both. Further, in some embodiments, the ultraviolet light source turns on only while the mouth piece is in the enclosure, the ultraviolet light source turns on only while the enclosure is closed, or both. Further still, in particular embodiments, the device for whitening teeth includes at least one Hall-effect sensor, for example, that controls whether the ultraviolet light source is on.

Various specific embodiments of a device for whitening teeth include a mouth piece and a sterilizer, for example, that sterilizes the mouth piece. In a number of embodiments, for example, the sterilizer sterilizes the mouth piece when the mouth piece is charging. Further, in many embodiments, the sterilizer operates only when the mouth piece is not in the user's mouth. Still further, in some embodiments, the device includes a safety mechanism, to protect the user, for instance, from the sterilizer. Even further, in various embodiments, the device for whitening teeth includes an enclosure that has a cover and the mouth piece is charged while the mouth piece is in the enclosure, the mouth piece is sterilized while the mouth piece is in the enclosure, or both. Further specific embodiments include various devices for whitening teeth that include at least one Hall-effect sensor. In a number of embodiments, for example, the device for whitening teeth includes a mouth piece and a charger. Still further, in various embodiments, the Hall-effect sensor detects whether the mouth piece is docked within the charger.

Moreover, some specific embodiments are or include a device for whitening teeth in a mouth of a user, where the device includes at least one sensor, for example, that senses whether the device is in the mouth of the user. In various embodiments, for example, the at least one sensor enables operation of the device only when the device is in the mouth of the user, the device includes a light and the operation of the device includes shining the light, the at least one sensor turns on the device when the device is placed in the mouth of the user, the at least one sensor includes an electro-magnetic field (EMF) array, or a combination thereof. Further, in some embodiments, the device includes a timer, for instance, that turns off the device after a certain amount of time, for example, that the device has been operating in the mouth of the user. Still further, in particular embodiments, the certain amount of time is adjustable, the certain amount of time is automatically adjusted (e.g., by the device), the certain amount of time is adjusted (e.g., by the device, for instance, automatically) based on color or shade of the teeth, or a combination thereof, as examples. Even further, in particular embodiments, the at least one sensor includes multiple sensors, for example, at multiple points on the device. Even further still, certain embodiments include a wakeup device, an accelerometer, or both (e.g., an accelerometer that serves as a wakeup device).

Further, various specific embodiments are or include a device for whitening teeth in a mouth of a user in which the device includes an electro-magnetic field (EMF) array. In some embodiments, for example, the electro-magnetic field (EMF) array senses whether the device is in the mouth of the user. Still further, in particular embodiments, the electro-magnetic field (EMF) array turns on the device when the device is placed in the mouth of the user, the electro-magnetic field (EMF) array turns off the device when the device is removed from the mouth of the user, the electro-magnetic field (EMF) array does not allow the device to operate when the device is not in the mouth of the user, or a combination thereof, as examples. Even further, some specific embodiments are or include a device for whitening teeth in a mouth of a user in which the device includes an accelerometer. For example, in particular embodiments, the accelerometer wakes up the device, for instance, when the device is shaken.

Still further specific embodiments are or include a device for whitening teeth of a user where the device outputs data. For example, in various embodiments, the device includes at least one sensor that collects the data for output from the device. Further, in a number of embodiments, the at least one sensor collects the data, the device whitens the teeth of the user (e.g., by shining light on the teeth of the user), or both, for instance, while at least part of the device is in the mouth of the user. Further still, in some embodiments, the device outputs the data wirelessly, for example, with Bluetooth. Even further, in various embodiments, the device outputs the data to a smart device, the device outputs the data to the Internet, the device outputs the data for computer analysis, or a combination thereof, as examples. Even further still, in particular embodiments, the data is processed with machine learning, the machine learning determines a duration for whitening the teeth, the machine learning determines an intensity for whitening the teeth, or a combination thereof, as examples. Still further, in a number of embodiments, the data includes a shade of the teeth, the data includes a color of the teeth, the data from the device is compared to data from other users to automatically determine a teeth-whitening treatment procedure for the user, or a combination thereof, as examples. Even further still, in certain embodiments, the device notifies the user of potential health risks associated with the teeth of the user, the device notifies the user of potential health risks associated with gums of the user, or both. Even further specific embodiments of a device for whitening teeth include at least one sensor and the device is controlled by a user using hand gestures detected by the at least one sensor. Still further specific embodiments of a device for whitening teeth include wireless charging in particular. Further, other embodiments are described herein.

BRIEF DESCRIPTION OF THE DRAWINGS

The drawings provided herewith illustrate, among other things, examples of certain aspects of particular embodiments. Other embodiments may differ. Various embodiments may include aspects shown in the drawings, described in the specification (including the claims), known in the art, or a combination thereof, as examples.

DETAILED DESCRIPTION OF EXAMPLES OF EMBODIMENTS

This patent application describes, among other things, examples of certain embodiments, and certain aspects thereof. Other embodiments may differ from the particular examples described in detail herein. Various embodiments are or include devices, apparatuses, machines, and methods for whitening teeth. In various embodiments, for example, light is used to whiten teeth. In many embodiments, a chemical is (e.g., also) used to whiten the teeth. In a number of embodiments, the light, or heat from the light, accelerates the whitening gel, for example, inside a closed system or mouth piece. Further various embodiments result in faster, more efficient, or longer lasting whitening, or a combination thereof, for instance, without the sensitivity of certain alternatives. Several examples are described herein, and different embodiments include one or more features from one or more of the examples described herein. All workable combinations are contemplated as different embodiments.

FIGS. 1 to 4 illustrate an example of an embodiment of a device or mouth piece for whitening teeth, device or mouth piece 100. In this embodiment, device 100 includes hand gesture control or sensor 105 (e.g., shown in FIG. 1) and LEDs 210 (e.g., shown in FIG. 2). In this embodiment, LEDs (light emitting diodes) 210 collectively form a light source that is located outside of the user's mouth when device 100 is properly positioned for operation, which is partially within the user's mouth. Light from LEDs 210 reflects off of polished surface or reflector 220 (e.g., shown in FIG. 2) to the user's teeth when device 100 is in operation.

Figure 2:
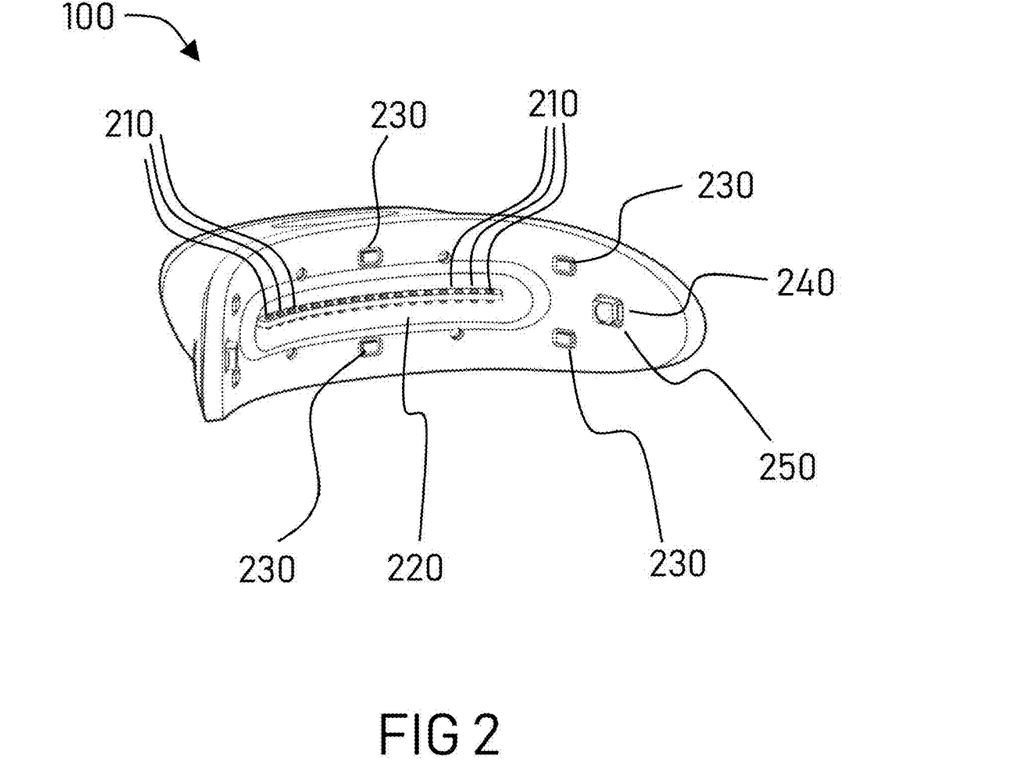
FIG. 2 is a rear perspective view of the example of an embodiment of a device or mouth piece for whitening teeth of FIG. 1, showing the side that faces, or extends into, the user's mouth.

In some embodiments, LEDs (e.g., 210) emit blue light. In certain embodiments, for example, the blue light has a wavelength of approximately 470 nm (nanometers) and is part of the "visible light spectrum", which ranges from approximately 400 nm to 700 nm. In various embodiments, the light (e.g., from LEDs 210) is harmless or has no known negative effect to the human body. Further, particular embodiments allow the customer or user to use the device (e.g., 100) or method for less-lengthy whitening sessions compared to other systems. Even further, in various embodiments, the serum formula works in conjunction with the light (e.g., from LEDs 210) to speed up whitening. Further still, in some embodiments, serum is refrigerated, for example, until delivered to customers, for instance, in warehouse facilities. This maintains the potency of the chemical compounds in various embodiments.

Figure 1:
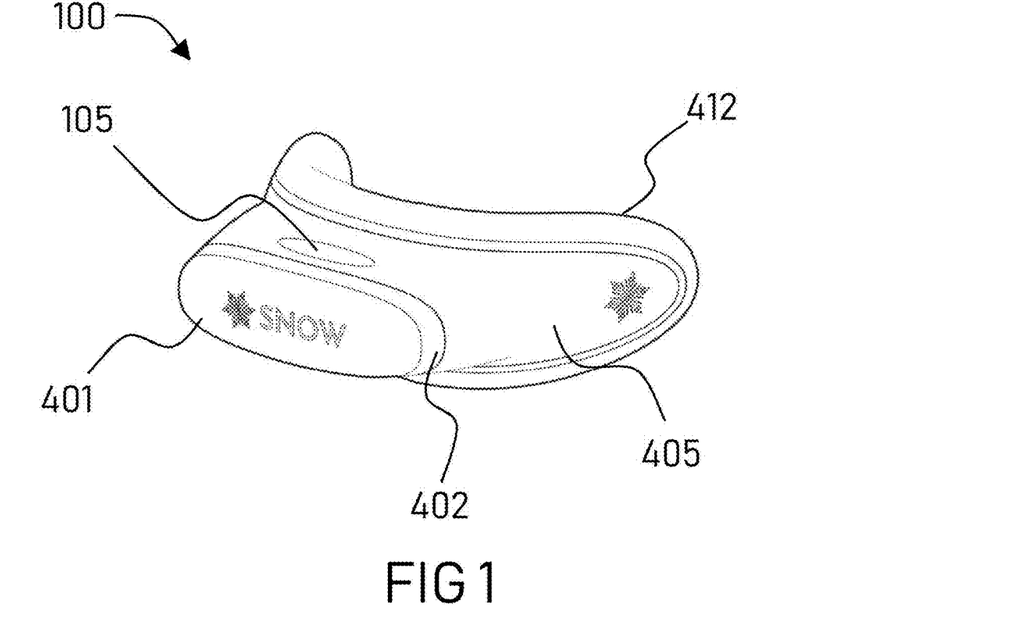
FIG. 1 is a front perspective view of an example of an embodiment of a device or mouth piece for whitening teeth.
Figure 3:
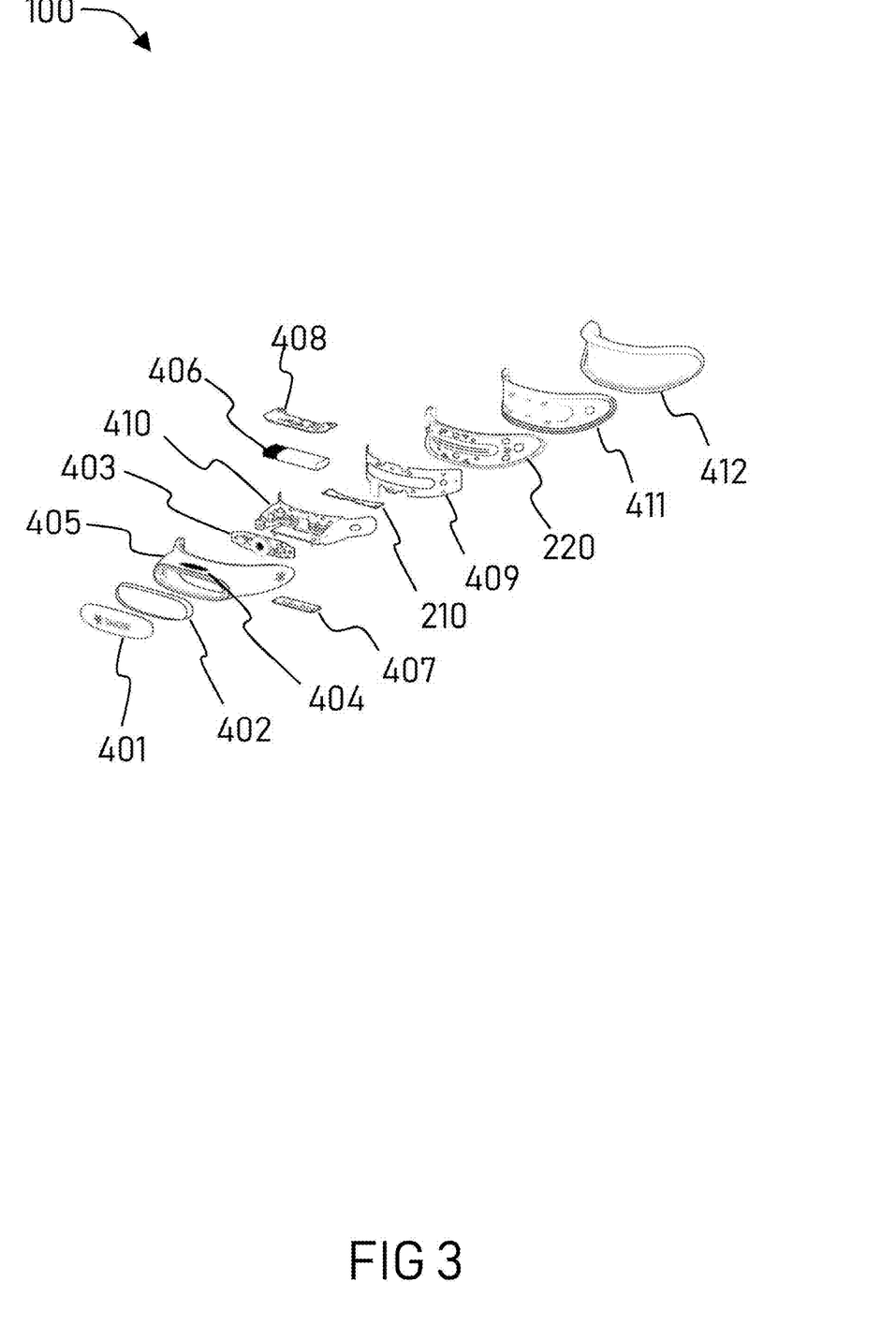
FIG. 3 is an exploded front view of the example of an embodiment of a device or mouth piece for whitening teeth, of FIGS. 1 and 2.
Figure 4:
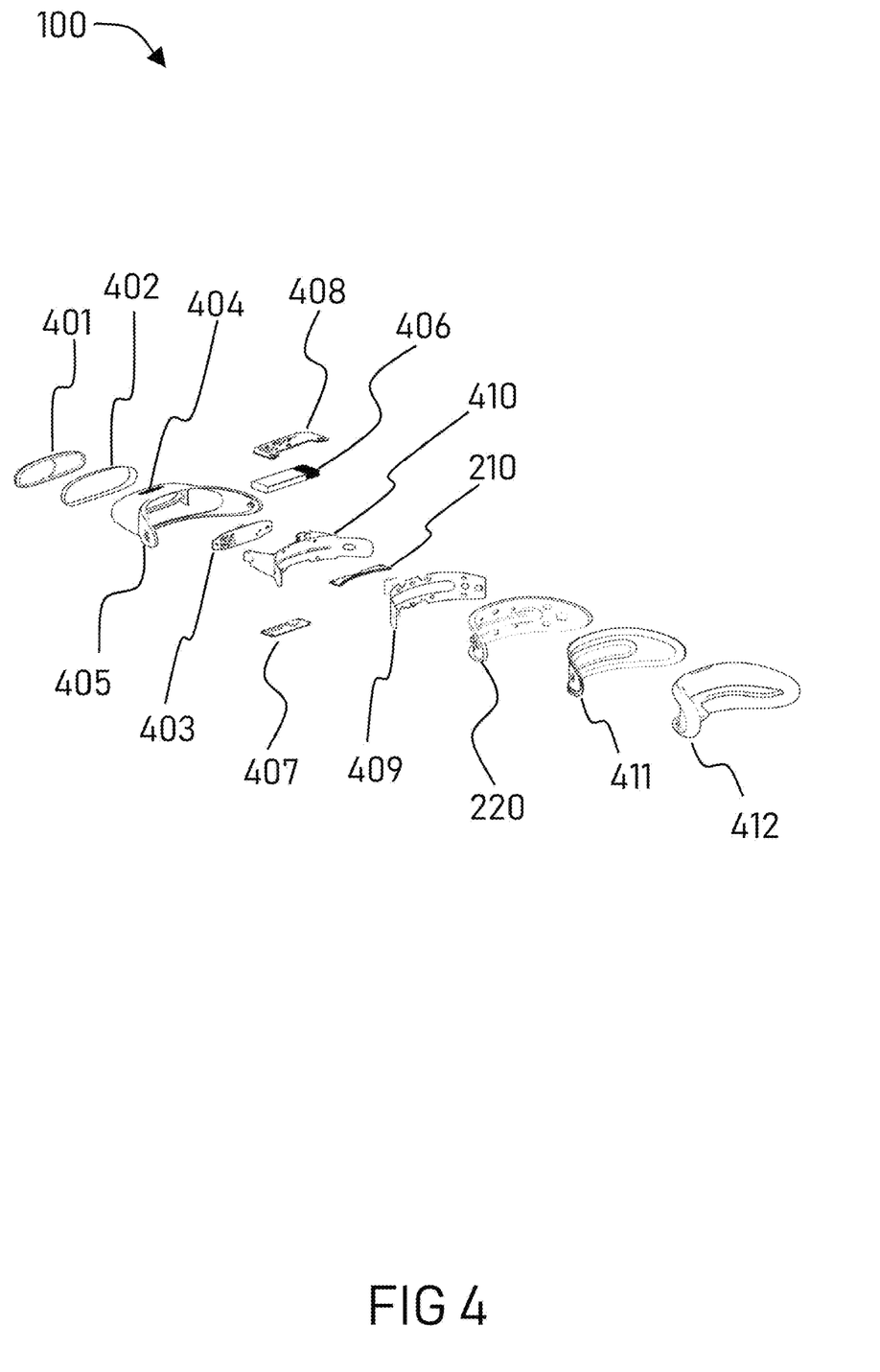
FIG. 4 is an exploded rear view of the example of an embodiment of a device or mouth piece for whitening teeth of FIGS. 1, 2, and 3.

As shown in FIGS. 3 and 4, in the embodiment illustrated, device or mouth piece 100 includes decorative front cover 401, decorative chrome band 402, wireless charging receiver PCB 403, motion detection lens 404, outer case 405, battery 406, LED sensors controls 407, gesture recognition and BLE PCB 408, self-cleaning UV LEDs and RGBW sensors 409, main hub 410 (e.g., that supports the PCBs), activating LEDs 210, LED reflector 220, clear LED water proof cover 411, and clear silicone mouth piece 412. Clear silicone mouth piece 412 is shown in FIG. 1 but omitted in FIG. 2 to better illustrate other components.

Activating Light Reflector

Summary of Problem: Prior designs of activating, elements require a flexible PCB and light elements within the mouth cavity. These source elements were fixed with no modulation schemes or intensity controls. In various embodiments, light (e.g., from LEDs 210 shown in FIGS. 2 to 4) is used to whiten teeth (e.g., in conjunction with chemical treatment). In a number of embodiments, however, it is necessary or beneficial to avoid using too much light.

Figure 8:
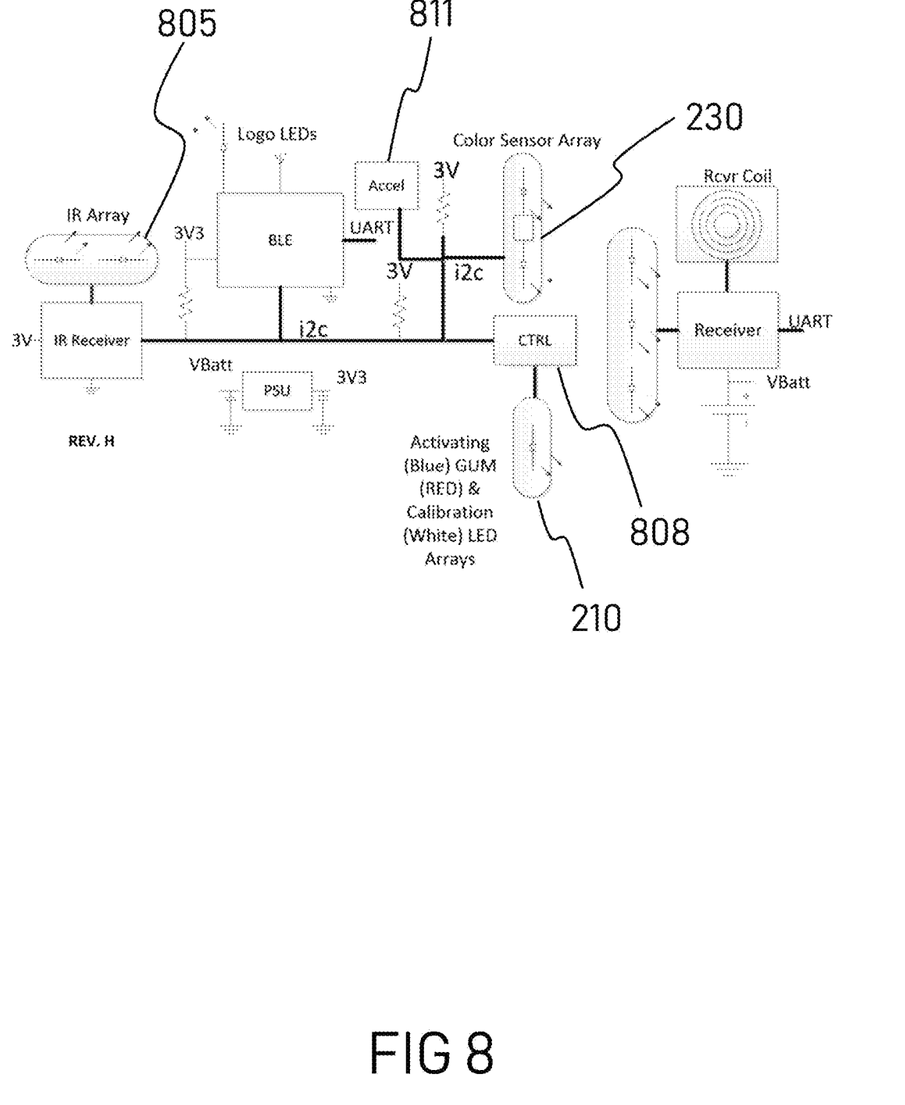
FIG. 8 is a schematic or block diagram showing how different electronic components are connected to each other in certain embodiments.

Solution: In a number of embodiments, a light reflection system (e.g., LEDs 210 and reflector 220) is controlled, for instance, via a pulse width modulation circuit (e.g., 808 shown in FIG. 8), for example, to control the grid and reflection pattern of a reflected light source (e.g., 210 or 210 and 220). In some embodiments, light reflection patterns are designed to change the intensity of the light waveform, for instance, by modifications to the peak output. Further, in particular embodiments, control mechanisms are done via wireless controls (e.g., Bluetooth), hand gestures (e.g., EMF—Electro-Magnetic Fields, IRF—Infrared Fields), or both. Still further, in certain embodiments, modulation schemes allow for power schemes of 0-100%, for example. An example of a device is device 100 shown in FIGS. 1 to 4, for instance. FIG. 8 is a schematic or block diagram showing how different electronic components are connected to each other in certain embodiments. Other embodiments may differ. Not necessarily every electrical connection or component is shown.

In various embodiments, the components of a reflector (e.g., 220) include a (e.g., chromed) reflective surface, for example, with an angled edge, for instance, to reflect light (e.g., from one or more LEDs, for instance, 210). Further, some embodiments, for example, include a reflector PCB, for example, that reflects light to (e.g., each of), for instance, six (6) quadrants of teeth. These quadrants may be, for example, in some embodiments: Center Top, Center Bottom, Left Top, Left Bottom, Right Top, and Right Bottom. In certain embodiments, the (e.g., LED) reflector PCB includes or consists of 6 arrays (e.g., of LEDs, for instance, 210), for example, independently controlled, for instance, to light each of the 6 quadrants. In turn, in some embodiments, the arrays or LEDs (e.g., 210) are driven, for example, by PWM (Pulse Width Modulation, e.g., 808), for instance, to alter the individual light intensity (e.g., in each quadrant). Further, in particular embodiments, the reflector (e.g., 220) is placed over a (e.g., flex) PCB.

In various embodiments, the reflector (e.g., 220) is made out of polished steel, chrome plating, or polished brass, as examples. Further, in a number of embodiments, the reflector (e.g., 220) is designed (e.g., shaped) to reflect light from outside of the users mouth (e.g., from LEDs 210), for example, evenly, for instance, throughout the center, left, and right sides of the user's mouth. In various embodiments, the light source (e.g., 210) is external to the mouth (i.e., when mouth piece 100 is properly positioned for treatment of the user's teeth) and the reflector (e.g., 220) reflects and distributes the light within the mouth. In a number of embodiments, this provides controlled distribution of the light, for example, in contrast with certain prior alternatives that do not guide the light at all.

In a number of embodiments, the light source (e.g., 210) is or includes LEDs, for example, discrete, RGB (red, green, blue), or both, for instance, which allows for variation in the frequency of the light in some embodiments. Further, an example of the pulse width modulation circuit is shown in FIG. 8 (e.g., 808 or TLC59108, for instance, connected to the LED arrays, for example, 210). In contrast with pulse width modulation (e.g., 808), other alternatives are On/Off. In a number of embodiments, the pulse width modulation circuit (e.g., 808) controls the grid and reflection pattern of the reflected light source (e.g., 210). In certain embodiments, for example, the PWM circuit (e.g., 808) works with the on-board intelligence of the mouth piece (e.g., 100). When the teeth are scanned, in some embodiments, an algorithm determines (e.g., based on the timer and shade value received for the quadrant), what duty cycle to set (e.g., for each quadrant), for instance, when the treatment begins. Due to the flexibility of the modulation scheme, in particular embodiments, the algorithm may be further tuned, for example, to generate modulation patterns to further enhance the treatment process, for instance, by the dynamic variation of the duty cycles for each quadrant. In certain embodiments, peak output (e.g., in terms of millicandela or mcd), or the intensity of light (e.g., from 210) or dynamic variations is controlled, for example, by the algorithm, driven by the PWM (e.g., 808), or both.

Further, in a number of embodiments, wireless control serves as a mechanism to utilize a third-party wireless device, for example, for setup, control, additional algorithms for analysis and treatment, or a combination thereof. Still further, in some embodiments, hand gestures are detected (e.g., via sensor 105) via electro-magnetic field (EMF) or infrared (IR), for instance, array 805 shown in FIG. 8), as examples. With an EMF solution, for instance, multiple antennas are set up in an array (e.g., sensor 105), in some embodiments, generating a field which can be manipulated by passing through the field with a hand or finger. In a number of embodiments, the antenna field is measured by the transmitter, and when a change is detected, the logic analyzes the condition. In various embodiments, for instance, the order of state changes determines the gesture to be achieved. For example: in a two antenna system (e.g., of sensor 105), if the left antenna triggered a state change, followed by the right antenna, the logic would assume that someone was swiping from left to right. Further, in certain embodiments, an IR solution works (e.g., in a similar way) using an array of IR transmitters (e.g., of sensor 105, for example, 805), for example, with an IR receiver centrally located within the array (e.g., 105 or 805). The example above also holds true for the IR solution (e.g., 805) in some embodiments. In a number of embodiments, hand gestures are read or detected by or at a mouth piece (e.g., 100, for instance, via sensor 105). Further, certain embodiments provide a simplified way to interact with a smart connected device. In particular embodiments, however, use of an app is avoided.

Various embodiments are or include a device (e.g., 100) for whitening teeth. Further, different embodiments include a light reflection system (e.g., light source 210 and reflector 220), a pulse width modulation circuit (e.g., 808 shown in FIG. 8), or both. Still further, in particular embodiments, the lighting system (e.g., 210) or light reflection system (e.g., 210 and 220) is controlled, for example, by the pulse width modulation circuit (e.g., 808). Even further, various embodiments include a reflected light source (e.g., 210 or 210 and 220). Moreover, in some embodiments, the pulse width modulation circuit (e.g., 808) controls a grid, a reflection pattern of the reflected light source, or both. Further still, in some embodiments, light reflection patterns are controlled, for instance, to change intensity of a light waveform, for example, by modifications to a peak output.

In various embodiments, a device (e.g., 100) for whitening teeth of a user includes a light source (e.g., 210) and a light delivery mechanism (e.g., reflector 220), for example, that delivers light from the light source (e.g., 210) to the user's teeth. In some such embodiments, for instance, the light source (e.g., 210) is driven by a pulse width modulation circuit (e.g., 808 shown in FIG. 8). Further, in a number of embodiments, the device (e.g., 100) includes a light source (e.g., 210) and a pulse width modulation circuit (e.g., 808) that drives the light source (e.g., 210). Still further, in various embodiments, the light source (e.g., 210) is located outside the user's mouth, the mechanism (e.g., reflector 220) that delivers light from the light source (e.g., 210) to the user's teeth is located within the user's mouth (i.e., when the device, e.g., 100, is in use), or both. Further still, in various embodiments, the mechanism that delivers light from the light source (e.g., 210) to the user's teeth is a reflector (e.g., 220), the light source includes LED's (e.g., 210), or both. Even further, in particular embodiments, the light source (e.g., 210) includes multiple (e.g., arrays of) light sources (e.g., 210), the multiple (e.g., arrays of) light sources are each independently controlled, the multiple (e.g., arrays of) light sources (e.g., 210) are each driven by pulse width modulation (e.g., 808), or a combination thereof, for example. Even further still, in some embodiments, the multiple (e.g., arrays of) light sources (e.g., 210) each primarily illuminate a different quadrant of the user's mouth, intensity of the multiple (e.g., arrays of) light sources (e.g., 210) is controlled, intensity of the light source (e.g., 210) is controlled (e.g., via PWM 808), or a combination thereof, as examples.

In a number of embodiments, the light source (e.g., 210) illuminates various (e.g., six) quadrants of the user's teeth. Further, in some embodiments, the light delivery mechanism (e.g., reflector 220) delivers light (e.g., from the light source, for instance, 210) to (e.g., six) quadrants of the user's teeth. For example, in particular embodiments, the (e.g., six) quadrants of the user's teeth are or include: Center Top, Center Bottom, Left Top, Left Bottom, Right Top, Right Bottom, or a combination thereof, as examples. Still further, in particular embodiments, the light delivery mechanism (e.g., 220) has an angled edge. Further still, in some embodiments, the device (e.g., 100) for whitening teeth further includes a printed circuit board. Even further, in certain embodiments, the light delivery mechanism (e.g., 220) is located over the printed circuit board, the printed circuit board is flexible, or both. Even further still, in particular embodiments, the light delivery mechanism (e.g., 220) delivers light (e.g., substantially evenly) from the light source (e.g., 210) to the user's teeth. In this context, "substantially" means to within plus or minus 25 percent.

In some embodiments, the light source (e.g., 210) is an RGB light source. Further, in some embodiments, the device (e.g., 100) is controlled wirelessly, for example, using a separate electronic device. For instance, in certain embodiments, the light source (e.g., 210), in particular, is controlled wirelessly using a separate electronic device. Still further, in some embodiments, the device (e.g., 100) is controlled using hand gestures (e.g., via sensor 105 shown in FIG. 1). For instance, in particular embodiments, the light source (e.g., 210) is controlled using hand gestures (e.g., detected by sensor 105). Even further, in some embodiments, the device (e.g., 100) includes a gesture sensor (e.g., 105), for example, for sensing the hand gestures. Further still, in certain embodiments, the device (e.g., 100) or gesture sensor (e.g., 105) includes two antennas, an infrared receiver (e.g., 805), or both.

In various embodiments of a device (e.g., 100) for whitening teeth of a user, the device includes a light source (e.g., 210) and a reflector (e.g., 220), the device includes a light source (e.g., 210) and a pulse width modulation circuit (e.g., 808 shown in FIG. 8), or both. Further, in various embodiments of a device (e.g., 100) for whitening teeth of a user, the device includes a light source (e.g., 210) and the light source is located outside the user's mouth (i.e., when the device is being used to whiten the teeth). Still further, in some embodiments, the device (e.g., 100) includes a light source (e.g., 210) that includes multiple (e.g., arrays of) light sources (e.g., 210) and the multiple (e.g., arrays of) light sources are each independently controlled. Further still, in various embodiments, a device (e.g., 100) for whitening teeth of a user is controlled wirelessly, for example, using a separate electronic device. For instance, in particular embodiments, the device (e.g., 100) includes a light source (e.g., 210) and the device is controlled wirelessly (e.g., using a separate electronic device). For example, in some embodiments, the light source (e.g., 210) is controlled wirelessly using a separate electronic device. Even further, in certain embodiments, a device (e.g., 100) for whitening teeth of a user is controlled using hand gestures (e.g., via sensor 105). For example, in some embodiments, the device (e.g., 100) includes a light source (e.g., 210) that is controlled using the hand gestures (e.g., via sensor 105). Even further still, in various embodiments, a device (e.g., 100) for whitening teeth of a user includes a light source (e.g., 210) and a gesture sensor (e.g., 105 shown in FIG. 1) for sensing hand gestures, the device (e.g., 100) includes two antennas, the device (e.g., 100) includes a gesture sensor (e.g., 105) that includes two antennas, the device (e.g., 100) includes a light source (e.g., 210) and a gesture sensor (e.g., 105) that includes two antennas, the device (e.g., 100) includes a light source (e.g., 210) and two antennas, or a combination thereof. Moreover, in some embodiments, a device (e.g., 100) for whitening teeth of a user includes; an infrared receiver, a gesture sensor (e.g., 105, for instance, that includes an infrared receiver), a light source (e.g., 210) and a gesture sensor (e.g., 105, for example, that includes an infrared receiver), a light source (e.g., 210) and an infrared receiver, or a combination thereof.

Visible Light Shade Detection System

Summary of Problem: Until now, the accuracy of determining the color or shade of a user's teeth has been a manual process, using both personal observation and shade guides provided by the dental community.

Solution: In various embodiments, the process of identifying the color or shade of teeth is automated. Further, in a number of embodiments, accuracy is improved over previous subjective methods in which color or shade was a matter of perspective. Still further, in various embodiments, (e.g., high accuracy) color sensors (e.g., 230 shown in FIG. 2) are used. In some embodiments, for example, these color sensors (e.g., 230) utilize red, green, blue, and white (RGBW) detection elements, as examples. Some embodiments are calibrated by using warm and cool colored white light sources, for instance (e.g., LEDs 210 shown in FIG. 2). In various embodiments, the sensors (e.g., 230) sense or analyze the reflected light from the target surface. In some embodiments, for example, the sensors (e.g., 230) sense color, while in other embodiments, the sensors (e.g., 230) sense shade, and in certain embodiments, the sensors (e.g., 230) sense both color and shade (e.g., of the teeth). Further, in certain embodiments, color or shade readings are output, for instance, over i2c, for example, in the value which references the visible light spectrum (390-700 nm). In a number of embodiments, the data is injected into a learning algorithm, for instance, running on a Host processor. Still further. In particular embodiments, this Host processor, for example, calculates the recommended treatment. Treatment settings for the Activating element are automatically populated, in some embodiments, for instance, when the device (e.g., 100) is in autonomous mode. Even further, in certain embodiments, the data is, output wirelessly (e.g., via Bluetooth), for example, connecting to an App, to the cloud (e.g., for detailed analysis), or both.

In various embodiments, calibration cool and warm light source elements (e.g., LEDs 210 shown in FIG. 2) are used in the calibration of the (e.g., color) sensor (e.g., 230). In some embodiments, for example, the warm and cool elements represent the color temperature of white light in the frequency spectrum necessary to achieve an accurate measurement of color. In particular embodiments, six (e.g., color) sensors (e.g., 230) are used, for example, in the locations shown. In some embodiments, RGBW sensors are used. Further, in some embodiments, six sensors (e.g., 230) translate to six individual grids, for example, three on top and three on the bottom. In certain embodiments, for instance, the configuration is designed to assign multiple quadrants to the mouth for analysis. In various embodiments, for example, the more sensors (e.g., 230), the more accurate the measurements will become, for instance, within each quadrant. In various embodiments, color data is collected from the teeth and used to control a teeth-whitening process, for instance, using a computer or a processor to analyze the color data. Further, particular embodiments use a computer or a processor to analyze the color data and control a teeth-whitening process (e.g., using the output from the computer or processor). Even further, in a number of embodiments, the "reflected light" is light originating from the teeth-whitening device (e.g., 100, for instance, from LEDs 210).

Certain embodiments use a learning algorithm to analyze color data, for example, to determine a treatment process. In a number of embodiments, for example, a recommended treatment includes, for example, an intensity, a duration, or both (e.g., of light emitted from LEDs 210). In various embodiments, the recommended treatment is different for different teeth. In various embodiments, the recommended treatment is calculated or determined, for example, based on compiled user data. Further, in some embodiments, a learning algorithm is used, for example, to allow the user to be hands off, let the hardware control the treatments, or both. Other embodiments, however, do not use a learning algorithm. Still further, different embodiments, use wireless or wired control, for example, of the hardware mechanisms.

Particular embodiments include, for example, sensor initialization, calibration, measurement, and data output. In some embodiments, an algorithm receives data output, calculates color, compares color to all quadrants, sets timer and peak intensity to each quadrant (e.g., based on shade color and delta between quadrants), or a combination thereof. In some embodiments, for example, data is output from the sensors (e.g., 230) over i2c to the host processor. Further, in some embodiments, data is input into the learning algorithm over I2c, for example, from sensors (e.g., 230), the cloud, and a smart device, for instance, running an application. Still further, in particular embodiments, sensor data and user data (e.g., from the cloud) is input into the learning algorithm. Examples include, in some embodiments, shade, color, serum strength, number of treatments per day, or a combination thereof. Even further, in some embodiments, feedback that is input into the learning algorithm to enable it to learn includes treatment times (e.g., in minutes), intensity, number of uses, shade data (e.g., at start of use to end of use), or a combination thereof. Even further still, in particular embodiments, output that is received from the learning algorithm includes device settings for treatment cycles, for example, intensity, duration, notifications (e.g., in the app), or a combination thereof. Moreover, in certain embodiments, output is used for treatments, enhancing the algorithm, or both. In various embodiments, treatment settings are or include intensity, duration, or both (e.g., of each quadrant).

Certain embodiments include a host processor, for example, a Master i2C controller for peripherals. Further, particular embodiments include an activating element, for example, blue LEDs (e.g., 210). Further still, in some embodiments, information is automatically populated, for example, from the hardware or from the App. Even further, some embodiments include an autonomous mode for example, that uses the machine learning, for instance, to set up the treatments. Still further, in some embodiments, other modes include gesture control, shake and wake, autonomous, wireless, or a combination thereof, as examples.

In various embodiments, a device (e.g., 100) for whitening teeth of a user includes one or more (e.g., color) sensors (e.g., 230 shown in FIG. 2), for example, used to analyze reflected light from a target surface of the teeth, for instance, to recommend a whitening treatment for the teeth. In a number of embodiments, for example, the device (e.g., 100) produces the light (e.g., with LEDs 210) that becomes the reflected light when reflected by the target surface of the teeth. Further, certain embodiments are or include a device (e.g., 100) for whitening teeth of a user that includes a (e.g., color or shade) sensor (e.g., 230), for instance, that detects color or shade of the teeth of the user. In a number of embodiments, a device (e.g., 100) for whitening teeth of a user detects color of the teeth of the user in particular. Still further, in various embodiments, a device (e.g., 100) for whitening teeth of a user collects color data from the teeth and controls a teeth-whitening process (e.g., operation of LEDs 210) using the color data.

In a number of embodiments, the device includes a computer or a processor (e.g., local or remote, in different embodiments), for example, that uses the (e.g., color, shade, or both) data, analyzes the data, controls the teeth-whitening process, or a combination thereof, as examples. In some embodiments, the device (e.g., 100) further includes a light source (e.g., 210), the device (e.g., 100) shines light on the teeth to whiten the teeth, or both. Further, in some embodiments, the device (e.g., including mouth piece 100) uses the color, shade, or both, of the teeth to determine how to whiten the teeth. Still further, in certain embodiments, the device uses the light reflected by the teeth to determine how to whiten the teeth. Even further, in particular embodiments, the device (e.g., 100) emits the light (e.g., with LEDs 210) that is reflected by the teeth, for instance, that is used by the device (e.g., including mouth piece 100) to determine how to whiten the teeth. Further still, in some embodiments, the device uses color, shade, or both, of the teeth to determine intensity of light to shine (e.g., with LEDs 210) onto the teeth, the device (e.g., including mouth piece 100) uses light reflected by the teeth to determine intensity of light to shine (e.g., with LEDs 210) onto the teeth, or both.

In some embodiments, the device (e.g., 100) for whitening teeth of a user includes cool light source elements (e.g., LEDs 210 shown in FIG. 2). Further, in some embodiments, the device (e.g., 100) includes warm light source elements (e.g., 210). Some embodiments include both. Moreover, in various embodiments, the light source elements (e.g., 210) are used to calibrate the device (e.g., 100). Still further, in some embodiments, the device (e.g., 100) for whitening teeth of a user includes (e.g., multiple) (e.g., color) sensors (e.g., 230). For example, in particular embodiments, different sensors (e.g., 230) sense light in different areas of the (e.g., user's) mouth. In certain embodiments, for instance, different (e.g., color) sensors (e.g., 230) sense light in different quadrants of the mouth. Further still, in a number of embodiments, the device includes a processor, for example, that controls the device (e.g., 100). For instance, in some embodiments, the processor controls the intensity of light produced (e.g., with LEDs 210) by the device (e.g., 100). Even further, in some embodiments, the processor analyzes reflected light from the teeth. For example, in particular embodiments, the processor analyzes color, shade, or both, of the teeth. Even further still, in certain embodiments, the device for whitening teeth of a user includes or uses a learning algorithm. For example, in some embodiments, the device uses the learning algorithm to analyze the (e.g., color) data, to control the teeth-whitening process (e.g., light from LEDs 210), or both.

Self Cleaning Mouth Guard

Summary of Problem: Prior designs in production offer a washable surface which leaves opportunities to grow bacteria and to cause infections within the user's mouth.

Figure 5:
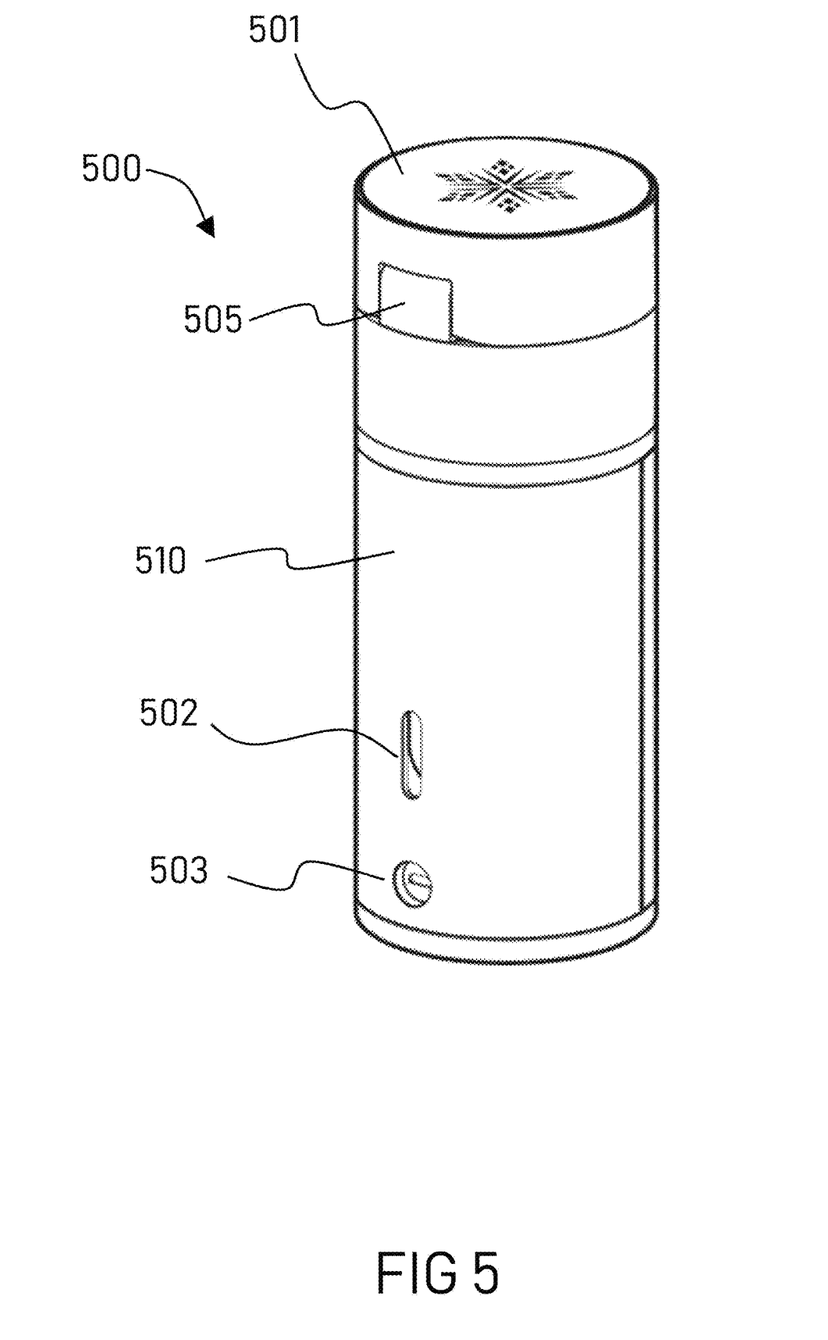
FIG. 5 is an isometric rear view of an example of an embodiment of a charging enclosure for the device or mouth piece for whitening teeth of FIGS. 1 to 4, shown with the cover closed.
Figure 6:
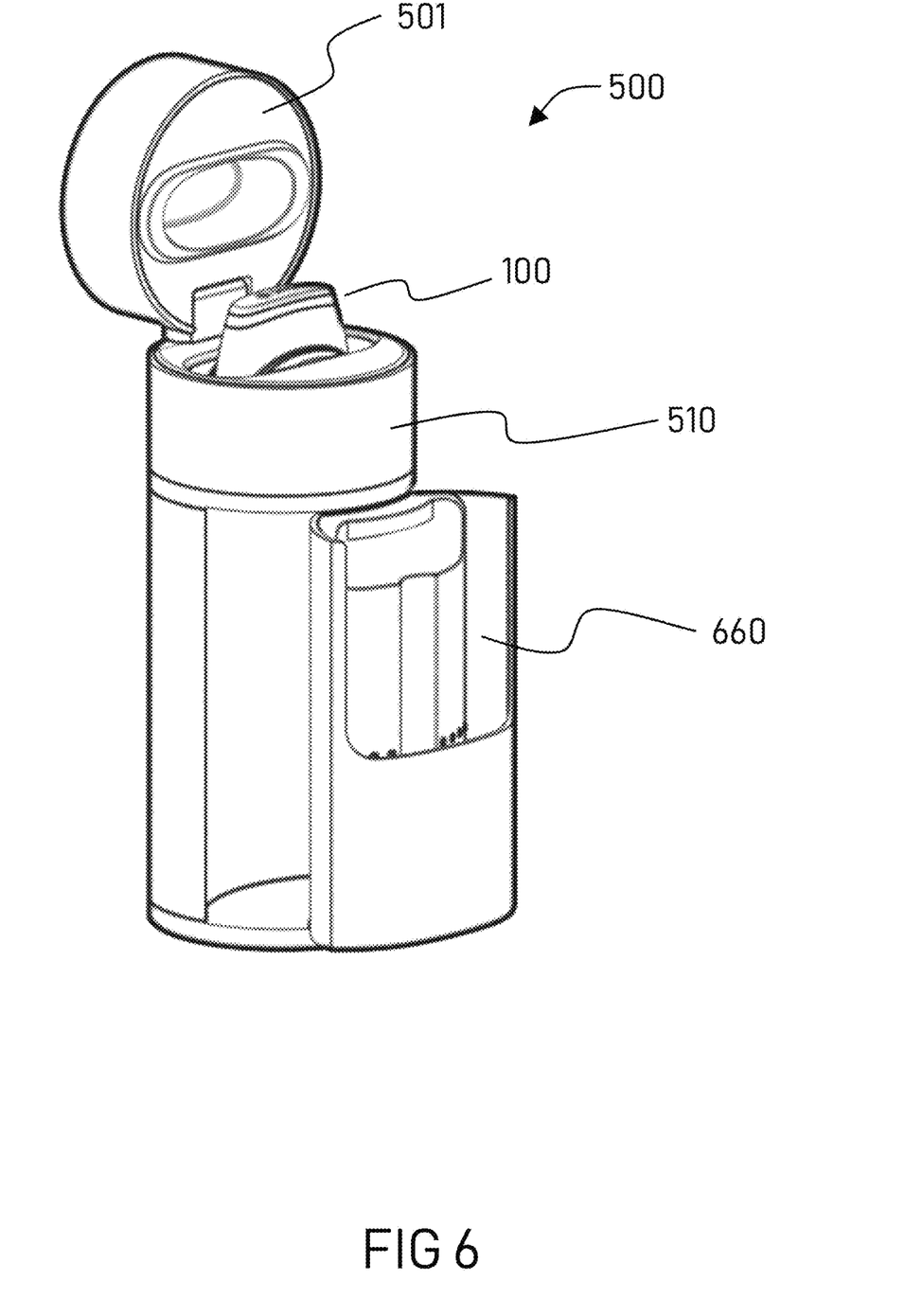
FIG. 6 is an isometric front view of the example of an embodiment of a charging, enclosure of FIG. 5 for the device or mouth piece for whitening teeth of FIGS. 1 to 4, shown with the cover open and the mouth piece docked in the enclosure.
Figure 7:
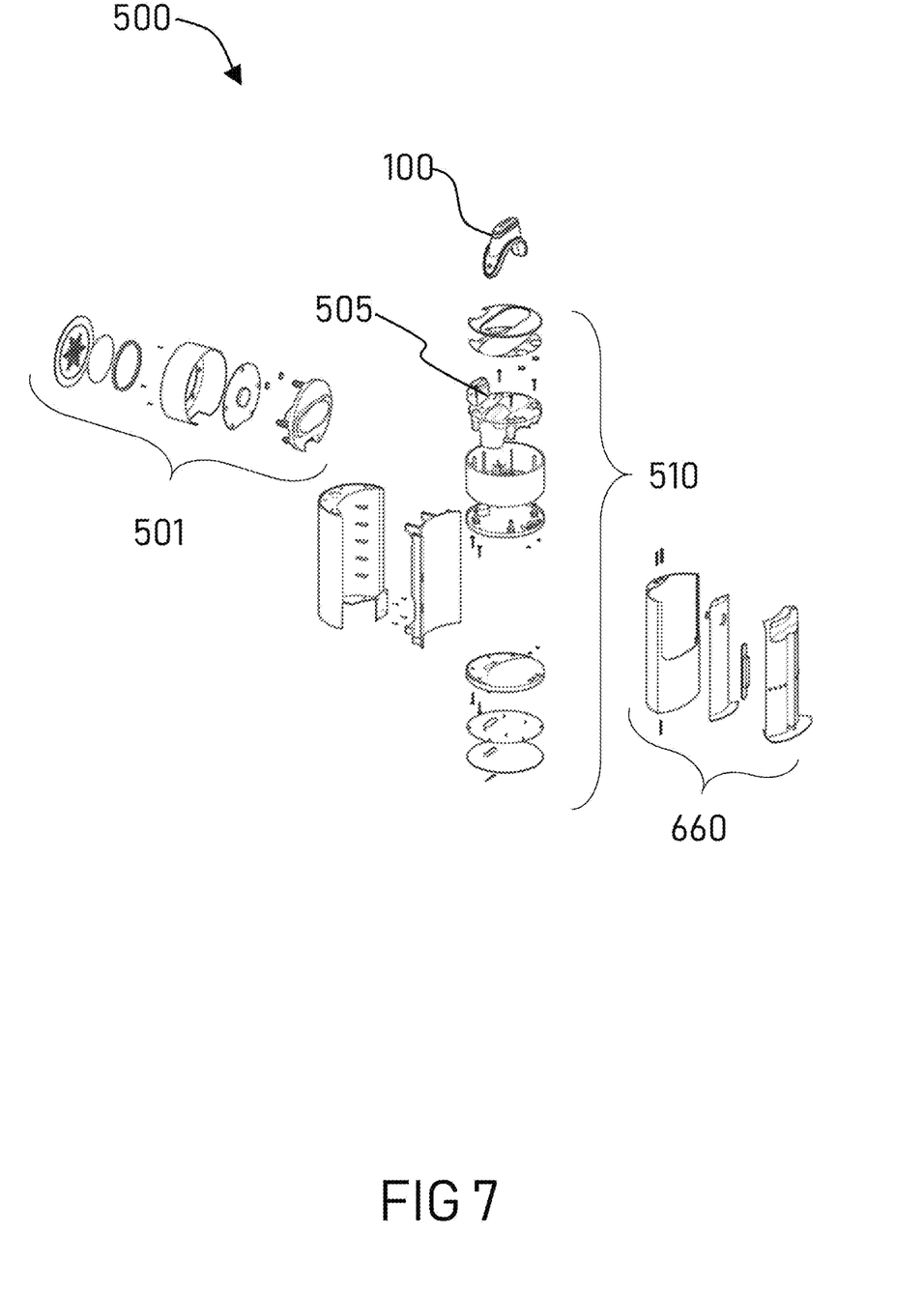
FIG. 7 is an exploded front view of the example of an embodiment of a charging enclosure of FIGS. 5 and 6 for the device or mouth piece for whitening teeth of FIGS. 1 to 4, shown with the cover in the open position and showing the mouth piece.

Solution: In a number of embodiments, ultraviolet light sources, for example, are embedded within the mouth guard, for instance, to clean the mouth piece when the user has finished using the product. For example, FIG. 2 shows UV light source elements 240 located in device, mouth piece, or mouth guard 100. In FIG. 2, two UV light source elements 240 are visible, but in some embodiments, a third UV light source element is present opposite the UV light source element 240 that is on the right side of FIG. 2. In some embodiments, the UV light source elements (e.g., 240) shine ultraviolet light on up to 100 percent of the mouth guard (e.g., 100) or the portion of the surface of the mouth guard that is in the mouth of the user when in operation. In various embodiments, utilization of a wireless charging system, and safety mechanisms to protect the users from damaging their eyes during the clean cycle, require that the mouth guard (e.g., 100) be successfully docked in an enclosure and the enclosure cover closed. FIG. 5 shows an example of an enclosure, enclosure 500, with cover 501 closed. In some embodiments, for example, the enclosure (e.g., 500) has a shape of a circular cylinder (e.g., as shown, for instance, cylindrical body 510), for example, with flat ends (e.g., at top and bottom) that are perpendicular or substantially perpendicular to a centerline of the cylinder. FIG. 5 shows excess cable storage 502, micro USB power connection 503, and cover hinge 505. FIG. 6 shows enclosure 500 with cover 501 open and mouth piece 100 docked inside enclosure 500 (e.g., for charging, sterilization, storage, or a combination thereof). In some embodiments, the cover (e.g., 501) has embedded charging circuits and BLE, magnetic latching, or a combination thereof, as examples. Further, FIG. 6 shows swing out serum wand and cable storage or swing door 660 (e.g., magnetic latching). In some instances herein, the word "device" refers to the mouth piece (e.g., 100) only, but in other instances, the word "device" may include the enclosure (e.g., 500) or charger. Further still, in certain instances, the word "device" may include a computing device, for example, that is in communication with the mouth piece (e.g., 100). Still further, these alternatives are not necessarily exhaustive.

In a number of embodiments, when the mouth piece (e.g., 100) has been successfully docked (e.g., in enclosure 500, for instance, as shown in FIG. 6), and the enclosure cover (e.g., 501) closed (e.g., as shown in FIG. 5), Hall effect sensors, for example, on two sides of the enclosure, trigger or enable the wireless charging system. This is an example of a safety mechanism that protects the user from eye damage from the ultraviolet light source. Once the transmitter has been enabled, in some embodiments, wireless charging protocol begins to transmit to the receiver, for instance, first checking for foreign objects in the path between the mouth guard (e.g., 100) and the enclosure (e.g., 500). In certain embodiments, once no objects are detected and the receiver has acknowledged communication, a timer on the receiver will trigger the UV elements (e.g., 240), for instance, for a particular time (e.g., X.xxxmS), which is a programmable timer in some embodiments. In particular embodiments, the UV elements (e.g., 240) are powered (e.g., directly) from the receiver side bridge and receiver, for instance, which keeps the elements (e.g., 240) from turning on accidentally.

Various embodiments (e.g., of a teeth-whitening device, for instance, 100) include one or more ultraviolet light sources (e.g., 240), for example, LEDs., for instance, to clean (e.g., sterilize) the teeth-whitening device (e.g., mouth piece, for instance, 100). Further, in various embodiments, the "ultraviolet light sources" (e.g., 240) are located in the wireless charging system, are driven by the wireless charging system, operate (e.g., sterilize or apply UV) while charging the (e.g., teeth-whitening) device (e.g., 100), or a combination thereof. Still further, certain embodiments include a safety mechanism, for example, to protect users from damaging their eyes during the cleaning cycle. Even further, particular embodiments, require that the mouth guard (e.g., 100) be successfully docked in an enclosure (e.g., 500) or that the enclosure cover (e.g., 501) be closed, for example, before charging the device (e.g., mouth guard 100), emitting UV (e.g., from UV lights 240), starting the cleaning cycle, or a combination thereof. Further still, some embodiments use one or more Hall effect sensors, for example, to trigger or enable a wireless charging system, a UV system (e.g., UV lights 240), or a sterilization or cleaning system (e.g., UV lights 240), as examples. The drawings show examples. In different embodiments, various wireless charging protocols are used.

Some embodiments include a receiver, for example, an Infineon solution. Further, certain embodiments check for foreign objects in the path between the mouth guard (e.g., 100) and the enclosure (e.g., 500), for example, by detecting heat changes, current, or both. Still further, in some embodiments, the receiver acknowledges communication using Qi. Even further, some embodiments include a timer, for example, that controls the amount of time that the UV elements (e.g., 240) or cleaning system is operated. In certain embodiments, the timer is adjustable, for instance, from 1-30 minutes. Even further still, in particular embodiments, the timer is set automatically, for example, using machine learning.

Various embodiments of a device for whitening teeth include a mouth piece (e.g., 100 shown in FIGS. 1 to 4, 6, and 7) and an ultraviolet light source (e.g., 240 shown in FIG. 2), for example, to clean the mouth piece (e.g., 100), for instance, when the user has finished using the device (e.g., 100). In a number of embodiments, for example, the mouth piece (e.g., 100) is cleaned with the ultraviolet light (e.g., from 240) while the device (e.g., 100) is charging. Further, in some embodiments, an ultraviolet light source (e.g., 240) sterilizes the mouth piece (e.g., 100). Still further, in particular embodiments, the device or ultraviolet light source (e.g., 240) sterilizes the mouth piece (e.g., 100) when the mouth piece (e.g., 100) is not in the user's mouth. Further still, in a number of embodiments, the device or ultraviolet light source (e.g., 240) sterilizes the mouth piece (e.g., 100) when, user has finished using the device (e.g., 100) for whitening the user's teeth, for example, when the mouth piece (e.g., 100) is charging. As used herein, "sterilizes" does not necessarily mean complete sterilization, but many embodiments significantly reduce the quantity of harmful or potentially harmful microorganisms from at least part of the device or mouth piece (e.g., 100).

A number of embodiments of a device for whitening teeth include a mouth piece (e.g., 100) and a sterilizer, for example, that sterilizes the mouth piece. In various embodiments, for instance, the sterilizer includes an ultraviolet light source (e.g., 240), the sterilizer sterilizes the mouth piece (e.g., 100) when the mouth piece is not in the user's mouth, the sterilizer sterilizes the mouth piece (e.g., 100) when user has finished using the device (e.g., 100) for whitening the user's teeth, the sterilizer sterilizes the mouth piece (e.g., 100) when the mouth piece (e.g., 100) is charging, or a combination thereof, as examples. Further, in many embodiments, a device (e.g., 100) for whitening teeth includes an ultraviolet light source (e.g., 240). Some embodiments include a mouth piece (e.g., 100) and an ultraviolet light source (e.g., 240), for example, combined. In a number of embodiments, for example, the ultraviolet light source (e.g., 240) sterilizes the mouth piece (e.g., 100), the ultraviolet light source (e.g., 240) operates when the mouth piece (e.g., 100) is not in the user's mouth, the ultraviolet light source (e.g., 240) operates only when the mouth piece (e.g., 100) is not in the user's mouth, the ultraviolet light source (e.g., 240) operates when the user has finished using the device (e.g., 100, for example, for whitening the user's teeth), the ultraviolet light source (e.g., 240) operates only when the user has finished using the device (e.g., mouth piece 100) for whitening the user's teeth, the ultraviolet light source (e.g., 240) operates when the mouth piece (e.g., 100) is charging, the ultraviolet light source (e.g., 240) operates only when the mouth piece (e.g., 100) is charging, or a combination thereof, as examples.

In various embodiments of the device (e.g., 100) for whitening teeth, the ultraviolet light source (e.g., 240) sterilizes at least a portion of the device (e.g., 100). Further, in some embodiments, the ultraviolet light source (e.g., 240) operates when the portion of the device (e.g., 100) is not in the user's mouth. Still further, in some embodiments, the ultraviolet light source (e.g., 240) operates only when the portion of the device (e.g., 100) is not in the user's mouth. Even further, in various embodiments, the ultraviolet light source (e.g., 240) operates when the user has finished using the device (e.g., 100) for whitening the user's teeth, for example, only when the user has finished using the device (e.g., 100) for whitening the user's teeth. Further still, in some embodiments, the ultraviolet light source (e.g., 240) operates when the device (e.g., 100) is charging (e.g., in enclosure 500), for instance, only when the device (e.g., 100) is charging. Even further still, in various embodiments, the device (e.g., 100) for whitening teeth includes the ultraviolet light source (e.g., 240) and the ultraviolet light source includes at least one LED, for example, that emits the ultraviolet light. Moreover, in a number of embodiments, the device for whitening teeth includes a wireless charging system (e.g., enclosure 500 or therein). Furthermore, in some embodiments, the ultraviolet light source (e.g., 240) is driven by the wireless charging system, the ultraviolet light source is located in the wireless charging system, the device (e.g., 100) includes a safety mechanism to protect the user from damaging their eyes with the ultraviolet light source, the device includes a safety mechanism to protect the user from damaging their eyes during a cleaning cycle, or a combination thereof, as examples. In various embodiments, the device includes a safety mechanism to protect the user during a cleaning cycle, the device includes a safety mechanism to protect the user while the device is charging, the device includes an enclosure (e.g., 500), the enclosure includes a cover (e.g., 501), or a combination thereof, as examples.

Moreover, in a number of embodiments, the device for whitening teeth includes a mouth piece (e.g., 100) and the mouth piece (e.g., 100) is charged while the mouth piece (e.g., 100) is in the enclosure (e.g., 500), the mouth piece (e.g., 100) is sterilized (e.g., with 240) while the mouth piece (e.g., 100) is in the enclosure (e.g., 500), or both. Further, in various embodiments, the device for whitening teeth includes an ultraviolet light source (e.g., 240) and the ultraviolet light source is located within the enclosure (e.g., 500), turns on while the mouth piece (e.g., 100) is in the enclosure (e.g., 500), turns on only while the mouth piece (e.g., 100) is in the enclosure (e.g., 500), turns on while the mouth piece (e.g., 100) is charging, turns on only while the mouth piece (e.g., 100) is charging, or a combination thereof. In various embodiments, for instance, the device (e.g., 100) for whitening teeth includes an ultraviolet light source (e.g., 240) and the ultraviolet light source turns on only while the enclosure (e.g., 500, for instance, cover 501) is closed. Still further, in a number of embodiments, the device includes a mouth piece (e.g., 100) and the mouth piece (e.g., 100) charges in the enclosure (e.g., 500) only when the enclosure (e.g., 500, for instance, cover 501) is closed, the mouth piece (e.g., 100) charges in the enclosure (e.g., 500) only when the mouth piece (e.g., 100) is successfully docked in the enclosure (e.g., 500), or both. Further still, in various embodiments, the device for whitening teeth includes a mouth piece (e.g., 100) and an ultraviolet light source (e.g., 240) and the ultraviolet light source only operates when the mouth piece (e.g., 100) is successfully docked in the enclosure (e.g., 500).

Further, in various embodiments, the device for whitening teeth includes at least one Hall-effect sensor. In a number of embodiments, for example, the at least one Hall-effect sensor is located in the enclosure (e.g., 500), the at least one Hall-effect sensor senses whether the enclosure (e.g., 500, for instance, cover 501) is closed, the at least one Hall-effect sensor senses whether the mouth piece (e.g., 100) is docked within the enclosure (e.g., 500), the at least one Hall-effect sensor controls whether the device (e.g., 100) charges, the at least one Hall-effect sensor controls whether the ultraviolet light source (e.g., 240) operates, the at least one Hall-effect sensor controls whether the sterilizer (e.g., 240) operates, or a combination thereof, as examples. Still further, in various embodiments, the device (e.g., 100) for whitening teeth includes a timer, for example, that controls how long the sterilizer (e.g., 240) operates, controls how long the ultraviolet light source (e.g., 240) operates, or both. Even further, in some embodiments, the timer is programmable.

Mouth Detection

Summary of Problem: Prior whitening systems are required to be plugged in or turned on before the device has been put into the user's mouth.

Solution: Various embodiments include one or multiple sensors or arrays that enable the function of the device (e.g., 100) once in the user's mouth. In some embodiments, for example, an EMF (Electro-Magnetic Field) Array (e.g., EMF field sensor or array 250 shown in FIG. 2) is placed (e.g., at three points) around the mouth guard (e.g., 100). In some embodiments, for instance, this requires the device (e.g., 100) to be in the mouth before operation. In addition, in particular embodiments, the array (e.g., 250) is enabled by using a wake on pick up feature, for instance, of an accelerometer (e.g., 811 shown in FIG. 8), to wake the device (e.g., 100) from a deep sleep. In some embodiments, hand gestures (e.g., detected via sensor 105) or the use of the App over a wireless (e.g., Bluetooth) connection begin the treatment cycle (e.g., operation of LEDs 210).

In prior whitening systems that were required to be plugged in or turned on before the device has been put into the user's mouth, this was a simple way to power the device, but there was no: intelligence for the user, modes of treatment, or a real sense of travel and portability, as examples.

In some embodiments, a user can put the device (e.g., 100) in her mouth and then turn it on or plug it in, but in particular embodiments, this may impact the results. In certain embodiments, for example, the timer starts once the activating LEDs (e.g., 20) are on. In various embodiments, an electro-magnetic field (EMF) array (e.g., via EMF field sensor or array 250 shown in FIG. 2) is used or included in a teeth-whitening device, for example, to detect whether the device (e.g., 100) is in someone's mouth. Further, in particular embodiments, the array (e.g, 250) is enabled by using a wake on pick up feature or an accelerometer (e.g., 811) to wake the device. In certain embodiments, for example, the accelerometer (e.g., 811) goes to an interrupt pin that can wake up the primary processor. In some embodiments, the device (e.g., 100) goes into a deep sleep, for example, an extremely low current state, for instance, to extend battery (e.g., 406 shown in FIGS. 3 and 4) life. Still further, in various embodiments, hand gestures (e.g., detected by sensor 105) are used. For example, in particular embodiments, hand gestures may include swiping (e.g., from left to right), pressing, finger twirling (e.g., like stirring coffee), or a combination thereof, as examples. Even further, in certain embodiments, wireless communication (e.g., Bluetooth) connects the device (e.g., 100) to a smart device, for example, a smart phone. In various embodiments, to begin a treatment cycle (e.g., energize LEDs 210), a user may use the App (e.g., on the smart device), use a gesture (e.g., detected by sensor 105), shake the device (e.g., mouth piece 100, accelerometer 811, or both), or a combination thereof, as examples.

In various embodiments, a device (e.g., 100) for whitening teeth includes at least one sensor or array (e.g., EMF sensor or array 250) that enables function of the device (e.g., 100) once the device (e.g., 100) is in the user's mouth and that requires the device (e.g., 100) to be in the mouth before operation. In a number of embodiments, for example, at least one sensor (e.g., 250) senses whether the device (e.g., 100) is in the user's mouth, turns on the device (e.g., 100) when the device is placed in the user's mouth, allows the device (e.g., 100) to operate only when the device (e.g., 100) is in the user's mouth, or a combination thereof. Further, various embodiments of a device (e.g., 100) for whitening teeth includes an electro-magnetic field (EMF) array (e.g., sensor or array 250 shown in FIG. 2). In some embodiments, for instance, the electro-magnetic field (EMF) array (e.g., 250) senses whether the device (e.g., 100) is in the user's mouth, turns on the device (e.g., 100) when the device (e.g., 100) is placed in the user's mouth, or both. Still further, in various embodiments, the at least one sensor (e.g., 250) turns off the device (e.g., 100) when the device (e.g., 100) is removed from the user's mouth, does not allow the device (e.g., 100) to operate when the device (e.g., 100) is not in the user's mouth, or both. Even further, in a number of embodiments, the device (e.g., 100) for whitening teeth includes a timer. In some embodiments, for example, the timer turns off the device (e.g., 100) after a certain amount of time that the device (e.g., 100) has been operating in the user's mouth. Further still, in particular embodiments, the certain amount of time is adjustable. Even further still, in some embodiments, the certain amount of time is automatically adjusted, for instance, by the device. For example, in certain embodiments, the certain amount of time is adjusted based on color (e.g., from sensors 230) of the user's teeth. Moreover, in certain embodiments, the certain amount of time is adjusted based on shade (e.g., from sensors 230) of the user's teeth.

Additionally, in various embodiments, the function or operation of the device (e.g., 100) includes shining a light (e.g., 210) in the user's mouth. For example, in a number of embodiments, turning on the device (e.g., 100) includes turning on a light (e.g., 210) in the user's mouth. Further, in various embodiments of a device (e.g., 100) for whitening teeth that has a light (e.g., 210), the light includes at least one LED. Still further, in various embodiments of a device (e.g., 100) for whitening teeth that includes at least one sensor (e.g., 250), the at least one sensor (e.g., 250) senses at multiple points on the device. For instance, in some embodiments, the at least one sensor (e.g., 250) includes multiple sensors at multiple points on the device (e.g., 100). For example, in particular embodiments, the at least one sensor (e.g., 250) senses at three separate points on the device (e.g., 100). Even further, in some embodiments, the at least one sensor (e.g., 250) senses at at-least three separate points on the device (e.g., 100). Further still, in certain embodiments, that include at least one sensor (e.g., 250), the at least one sensor (e.g., 250) is or includes an array. For instance, in particular embodiments that include an array (e.g., 250), the array (e.g., 250) is used to detect whether the device (e.g., 100) is in a user's mouth. Even further still, in certain embodiments that include an array, the array is an electro-magnetic field (EMF) array (e.g., via EMF field sensor or array 250 shown in FIG. 2).

In a number of embodiments of a device for whitening teeth, the device (e.g., 100) operates in a deep sleep, for example, before being turned on, before being placed in the user's mouth, or both. Further, certain embodiments include a wakeup device (e.g., 811). Moreover, some embodiments of a device (e.g., 100) for whitening teeth include an accelerometer (e.g., 811). In some embodiments, for example, the accelerometer (e.g., 811) wakes up the device (e.g., 100). Still further, various embodiments of a device for whitening teeth include a processor. Further still, in certain embodiments, the wakeup device or accelerometer (e.g., 811) is connected to an interrupt pin on the processor of the device. Even further, in some embodiments, the device (e.g., 100) for whitening teeth is controlled with hand gestures (e.g., detected by sensor 105), though a wireless connection to a smart device, or though Bluetooth (e.g., by a smart device), as examples. In various embodiments, a device (e.g., 100) for whitening teeth is controlled with a smart device. Even further still, in some embodiments, the device (e.g., 100) for whitening teeth is controlled by shaking the device (e.g., detected by accelerometer 811). For example, in some embodiments, the device (e.g., 100) is woken up by shaking the device (e.g., 100). Furthermore, in particular embodiments, a treatment cycle is started by shaking (e.g., detected by accelerometer 811) the device (e.g., 100), by making a hand gesture (e.g., detected by sensor 105), with a smart device, by a combination of these, or by any of a combination of these, for example, selected by the user.

Wireless Dental Whitening System

Summary of Problem: Prior whitening systems do not take advantage of machine learning or a user's specific needs.

Solution: In a number of embodiments, a wireless connected system includes one or multiple sensor arrays (e.g., 230), for example, that output data (e.g., over Bluetooth) to a smart device, and, in some embodiments, (e.g., finally) to the cloud, for instance, for analysis. In particular embodiments, the device (e.g., also) has one or more (e.g., embedded) machine learning algorithms, for example, using both a primary and secondary host processors. Additional Flash memory, in particular embodiments, allows for storage and computation methods for treatment and user recommendations. Further, in particular embodiments, the system is (e.g., also) user customizable, for example, using an iOS or Android app, for instance, to set a manual treatment, review scan results, recommended treatments, treatment schedules, naming the device, RGB esthetic customizable LEDs, or a combination thereof. Still further, in particular embodiments, (e.g., multiple) safety features are also included, for example, with the self-cleaning feature (e.g., 240), for instance, to ensure that the device (e.g., 100) is (e.g., adequately) free from bacteria when properly stored. Even further, in particular embodiments, (e.g., multiple) inputs (e.g., 105) to the mouth guard (e.g., 100) allow users (e.g., that are less tech savvy) to utilize (e.g., simple) hand gestures to operate the device (e.g., 100), for example, using infrared (e.g., 805) and/or electromagnetic field array(s).

Various embodiments address user's specific needs that prior whitening systems do not necessarily address. Further, a number of embodiments take advantage of technology that prior whitening systems do not necessarily take advantage of. For example, various embodiments include wireless charging (e.g., in enclosure 500), treatments that users can track, machine learning (e.g., that helps improve performance), self-cleaning (e.g., using UV elements 240), shade detection (e.g., with sensors 230), wireless control, connection to the cloud, or a combination thereof. Further, in a number of embodiments, a teeth-whitening device (e.g., 100) is Internet connected. Still further, in some embodiments, a teeth-whitening device (e.g., 100) outputs data (e.g., via Bluetooth), for example, to a smart device, for (e.g., computer) analysis, to the cloud (e.g., cloud services, for machine learning and analysis, for notification of users of potential health risks, for instance, with their teeth and/or gums), or a combination thereof, as examples.

In different embodiments, various types of sensor arrays are used. Examples of sensors include electro-magnetic field sensors (e.g., 250), infrared sensors (e.g., 805), color or shade sensors (e.g., 230), and hydrogen sulfide sensors (H2S). Further, different types of smart devices that can be used include phones, iPods, tablets, watches, and TVs. Still further, in some embodiments, machine learning algorithms are used. In particular embodiments, for example, data from the mouth piece (e.g., 100) is uploaded to the cloud and compared to other users, progress, and settings. Further still, in certain embodiments, for example, based on treatment outcomes, the device (e.g., 100) can auto-configure, for instance, for desired results. Even further, certain embodiments include primary and secondary host processors. For example, in some embodiments, the primary processor is an Arm Cortex M-4, the secondary process is PIC MCU, or both. In various embodiments, the primary processor is used for local methods and more-complex methods are processed in the cloud, for example. Even further still, in some embodiments, systems are user customizable. In particular embodiments, for example, users can set their own treatments, customize: timers, intensity, duration, or programs, or a combination thereof, for instance, to cycle between teeth whitening and gum treatment.

In a number of embodiments, a device (e.g., 100) for whitening teeth include at least one sensor (e.g., 105, 230, or both). Further, in various embodiments, the device wirelessly outputs data from the at least one sensor (e.g., 230), for example, to a smart device. Still further, in some embodiments, the device (e.g., 100) wirelessly outputs data from the at least one sensor (e.g., 230) to the cloud, for instance, for analysis. Further still, in some embodiments, the device (e.g., 100) is controlled by a user using hand gestures, for example, detected by the at least one sensor (e.g., 105). Even further, in many embodiments, a device (e.g., 100) for whitening teeth includes wireless charging (e.g., in enclosure 500), self cleaning (e.g., with UV elements 240), machine learning, or a combination thereof, as examples. Even further still, in certain embodiments, the machine learning determines a duration, for example, for whitening the teeth (e.g., by operating LEDs 210), the machine learning determines an intensity, for instance, for whitening the teeth, or both. Moreover, in particular embodiments, the machine learning uses shade of the teeth, the machine learning uses color of the teeth (e.g., detected by sensors 230), or both. In various embodiments, a device for whitening teeth includes color or shade detection (e.g., using sensors 230).

Furthermore, in a number of embodiments, a device (e.g., 100) for whitening teeth outputs data, outputs data wirelessly, outputs data with Bluetooth, outputs data to a smart device, outputs data for computer analysis, is connected to the Internet, is connected to the cloud, outputs data for cloud services, outputs data for machine learning, or a combination thereof, as examples. In some embodiments, for example, the device (e.g., 100) notifies users of potential health risks, for example, with their teeth, with their gums, or both. Moreover, in particular embodiments, the potential health risks are identified in the computer analysis. Further, in various embodiments, the at least one sensor is a sensor array, the device for whitening teeth includes: an electromagnetic field sensor (e.g., 250), an infrared sensor (e.g., 805), a color or shade sensor (e.g., 230), a hydrogen sulfide sensor, or a combination thereof, as examples. Still further, in some embodiments, the smart device is or can be a phone, the smart device is or can be a tablet computer, the smart device is or can be an iPod, the smart device is or can be a watch, the smart device is or can be a TV, or a combination thereof, as further examples. Further still, in various embodiments, data from the device (e.g., 100) is compared to or analyzed with data from other users. For example, in particular embodiments, data from the device (e.g., 100) is compared to data from other users to automatically determine a treatment procedure (e.g., for the current user, other users, or both).

In various embodiments, the device includes a primary host processor, includes a secondary host processor, includes an Arm Cortex M-4 processor, includes a PIC MCU processor, or a combination thereof, as examples. Further, in many embodiments, users can set (e.g., select) their own treatments. For example, in particular embodiments, users can set a timer, users can set intensity of a treatment, users can set duration of a treatment, or a combination thereof. Further still, in various embodiments, users can select a teeth-whitening treatment, users can select a gum treatment, users can cycle between teeth-whitening and gum treatments, or a combination thereof, as examples.

Still other embodiments include various methods, for example, of performing functions described herein. Each method, for example, includes at least certain acts. Various embodiments include an apparatus or method of obtaining or providing an apparatus or information, for instance, that include a novel combination of the features described herein. Even further embodiments include at least one means for accomplishing, at least one functional aspect described herein. The subject matter described herein includes various means for accomplishing the various functions or acts described herein or that are apparent from the structure and acts described. Each function described herein is also contemplated as a means for accomplishing that function, or where appropriate, as a step for accomplishing that function. Moreover, various embodiments include certain (e.g., combinations of) aspects described herein. All novel combinations that are feasible are potential embodiments. Some embodiments may include a subset of elements described herein and various embodiments include additional elements as well.

Further, various embodiments of the subject matter described herein include various combinations of the acts, structure, components, and features described herein, shown in the drawings, described in any documents that are incorporated by reference herein, or that are known in the art. Moreover, certain procedures can include acts such as manufacturing, obtaining, or providing components that perform functions described herein or in the documents that are incorporated by reference. Further, as used herein, the word "or", except where indicated otherwise, does not imply that the alternatives listed are mutually exclusive. Even further, where alternatives are listed herein, it should be understood that in some embodiments, fewer alternatives may be available, or in particular embodiments, just one alternative may be available, as examples.

What is claimed is:

1. A teeth whitening kit, comprising:
    a mouthpiece configured to be positioned in a user's mouth such that an inner surface extends adjacent at least a portion of a user's teeth, the mouthpiece having a whitening light source configured to deliver light along the portion of the user's teeth adjacent the inner surface of the mouthpiece for whitening the teeth, and an ultraviolet light source; and
    an enclosure configured to receive the mouthpiece therein, and a cover movable between an open configuration for allowing insertion of the mouthpiece into the enclosure, and a closed configuration configured to fully enclose the mouthpiece within the enclosure, wherein the enclosure is configured to activate the ultraviolet light source upon movement of the cover to the closed configuration to initiate a disinfection procedure.

2. The kit of claim 1, wherein the disinfection procedure is initiated for a predetermined time period.

3. The kit of claim 1, wherein the enclosure includes a sensor that detects when the cover is moved from the open configuration to the closed configuration.

4. The kit of claim 1, wherein the enclosure includes a wireless charging system configured to wirelessly charge the mouthpiece when the mouthpiece is disposed within the enclosure, and wherein the wireless charging system initiates a charging cycle upon movement of the cover to the closed configuration.

5. The kit of claim 1, wherein the ultraviolet light source can only be activated when the cover is in the closed configuration.

6. The kit of claim 1, wherein the wireless charging system drives the ultraviolet light source.

7. The kit of claim 1, wherein the ultraviolet light source is positioned on an inner surface of the mouthpiece.

8. A teeth whitening kit, comprising:
    a mouthpiece configured to be positioned in a user's mouth such that an outer case coupled to the mouthpiece projects outward from the user's mouth, the outer case including a plurality of light-emitting diodes configured to emit blue light and a battery configured to provide power to the plurality of light-emitting diodes, and the mouthpiece including a reflector disposed thereon and configured to evenly distribute the blue light from the plurality of light-emitting diodes along the user's teeth;
    an enclosure having a wireless charging system therein, the enclosure being configured to receive the mouthpiece and to wirelessly charge the battery in the mouthpiece; and
    an ultraviolet light source positioned in the mouthpiece, the ultraviolet light source being configured to deliver ultraviolet light to the mouthpiece for disinfecting the mouthpiece, and the ultraviolet light source being activatable only when disposed within the enclosure.

9. The kit of claim 8, wherein the enclosure includes a sensor for detecting when the mouthpiece is disposed therein.

10. The kid of claim 8, wherein the enclosure is configured to automatically activate the ultraviolet light source when the mouthpiece is disposed therein.

11. The kit of claim 10, wherein the enclosure is configured to automatically activate the ultraviolet light source for a predetermined period of time.

12. The kit of claim 8, wherein the enclosure includes a cover configured to fully enclose the mouthpiece within the enclosure.

13. The kit of claim 8, wherein the enclosure is cylindrical.

* * * * *